United States Patent
Liu et al.

(10) Patent No.: US 11,618,902 B2
(45) Date of Patent: Apr. 4, 2023

(54) BACILLUS SUBTILIS FOR PRODUCING N-ACETYLNEURAMINIC ACID AND APPLICATION THEREOF

(71) Applicant: Jiangnan University, Wuxi (CN)

(72) Inventors: Yanfeng Liu, Wuxi (CN); Long Liu, Wuxi (CN); Xiaolong Zhang, Wuxi (CN); Guocheng Du, Wuxi (CN); Jianghua Li, Wuxi (CN); Jian Chen, Wuxi (CN)

(73) Assignee: Jiangnan University, Wuxi (CN)

( * ) Notice: Subject to any disclaimer, the term of this patent is extended or adjusted under 35 U.S.C. 154(b) by 137 days.

(21) Appl. No.: 17/176,313

(22) Filed: Feb. 16, 2021

(65) Prior Publication Data
US 2021/0171962 A1    Jun. 10, 2021

(30) Foreign Application Priority Data

Mar. 30, 2020 (CN) .......................... 202010237111.X
Mar. 30, 2020 (CN) .......................... 202010237125.1
Mar. 30, 2020 (CN) .......................... 202010238268.4

(51) Int. Cl.
*C12N 1/20* (2006.01)
*C12N 15/75* (2006.01)
*C12P 19/26* (2006.01)
*C12R 1/25* (2006.01)

(52) U.S. Cl.
CPC ............. *C12N 15/75* (2013.01); *C12N 1/205* (2021.05); *C12P 19/26* (2013.01); *C12R 2001/25* (2021.05)

(58) Field of Classification Search
CPC ...................................................... C12N 15/75
See application file for complete search history.

(56) References Cited

U.S. PATENT DOCUMENTS

2007/0231342 A1* 10/2007 Giuliani .................. A61P 31/04
                                                                  424/190.1
2020/0332325 A1* 10/2020 Jennewein ............... C07H 3/08

FOREIGN PATENT DOCUMENTS

| CN | 106929461 A | * | 7/2017 | ............. C12N 15/75 |
| CN | 107604025 A | * | 1/2018 | |
| CN | 108441461 A | * | 8/2018 | ............. C12N 15/75 |

* cited by examiner

*Primary Examiner* — Albert M Navarro
*Assistant Examiner* — Mark Navarro
(74) *Attorney, Agent, or Firm* — IPro, PLLC

(57) ABSTRACT

The disclosure discloses *Bacillus subtilis* for producing N-acetylneuraminic acid and application thereof, and belongs to the field of genetic engineering. The disclosure optimizes the expression levels of key enzymes in N-acetylneuraminic acid synthesis pathways on genome through promoters of different strength, reduces the protein synthesis pressure caused by the expression of enzymes on cells, and further integrates the three N-acetylneuraminic acids in a same *Bacillus subtilis* engineering strain. *Bacillus subtilis* with improved N-acetylneuraminic acid production is obtained, and the production reaches 10.4 g/L at the shake flask level, laying a foundation for further improving the NeuAc production from *Bacillus subtilis*.

11 Claims, 1 Drawing Sheet
Specification includes a Sequence Listing.

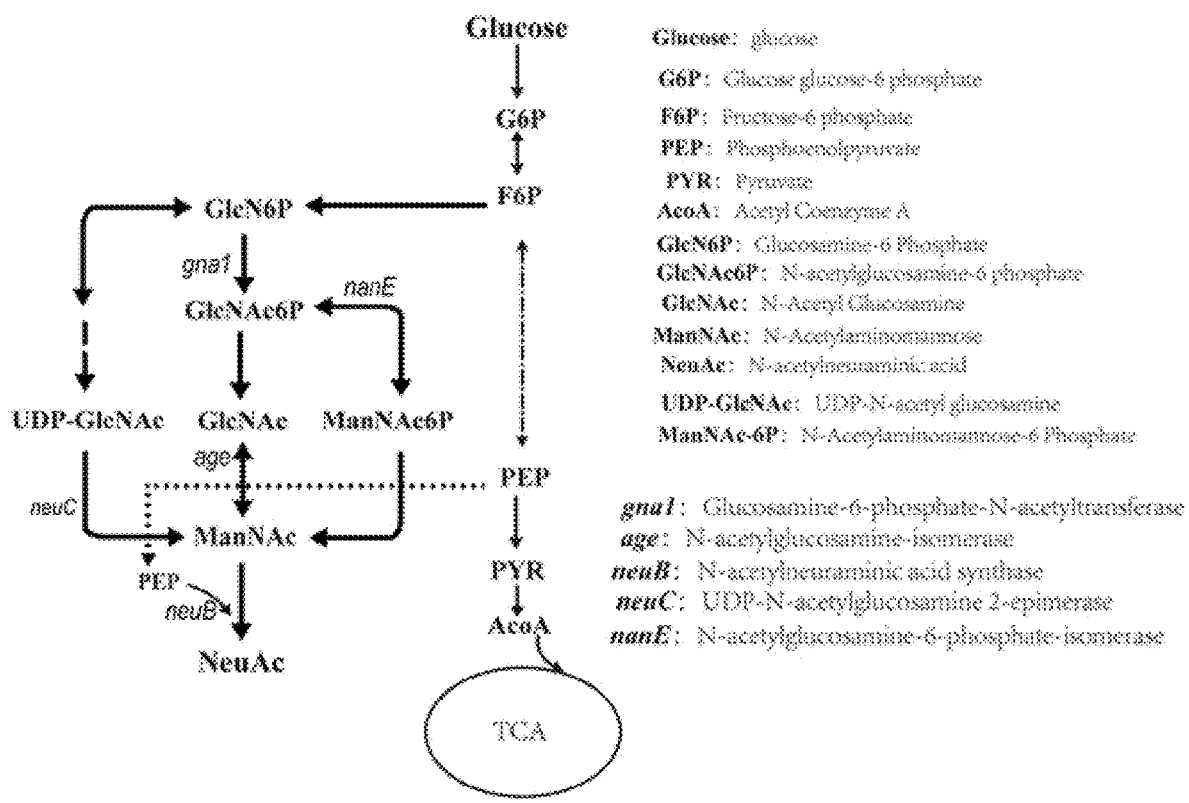

BACILLUS SUBTILIS FOR PRODUCING N-ACETYLNEURAMINIC ACID AND APPLICATION THEREOF

REFERENCE TO SEQUENCE LISTING

The instant application contains a Sequence Listing in TXT format as a file named "3050-0199-YGHY2020-28-Seq.txt", created on Jan. 27, 2021, of 44 kB in size, and which is hereby incorporated by reference in its entirety.

TECHNICAL FIELD

The disclosure relates to *Bacillus subtilis* for producing N-acetylneuraminic acid and application thereof, and belongs to the field of genetic engineering.

BACKGROUND

N-acetylneuraminic acid is a functional monosaccharide, which is widely found in microorganisms and mammals. In the human body, N-acetylneuraminic acid is involved in many physiological processes such as cell recognition and signal transduction. Therefore, N-acetylneuraminic acid is widely used to enhance infant immunity and promote infant brain development. At present, N-acetylneuraminic acid is mainly extracted from natural products (eggs, bird's nests, etc.), but the method has the defects that other products are difficult to separate and the cost is high. In addition, N-acetylneuraminic acid can be obtained by a method of whole cell transformation, but the method requires the high-cost substrates acetylglucosamine and pyruvate, resulting in higher cost.

*Bacillus subtilis* is a widely used production host for food enzyme preparations and important nutritional chemicals, and the products of *Bacillus subtilis* have been approved by the FDA as a "generally regarded as safe" (GRAS) level. Therefore, it is an effective strategy to efficiently synthesize N-acetylneuraminic acid with *Bacillus subtilis* as the host by using cheap carbon sources such as glucose as the substrate through metabolic engineering modification.

At present, the N-acetylneuraminic acid metabolic pathway constructed in *Bacillus subtilis* is mainly through an NeuC key enzyme synthesis pathway with UDP-N-acetylglucosamine as a precursor, an Age key enzyme synthesis pathway with N-acetylglucosamine as a precursor, and an NanE key enzyme synthesis pathway with N-acetylglucosamine-6 phosphate as the precursor. Since the pathways involve many foreign enzyme proteins, the introduction of multiple enzyme proteins at the same time can easily cause cell pressure, which is not conducive to cell growth and product synthesis. Therefore, a multi-pathway compounding strategy is difficult to achieve, which severely limits the increase in the production of N-acetylneuraminic acid and further limits the market application thereof.

SUMMARY

The disclosure provides recombinant *Bacillus subtilis* expressing glucosamine-6-phosphate-N-acetyltransferase (Gna1), N-acetylglucosamine isomerase (Age) and N-acetylneuraminic acid synthase (NeuB).

In one embodiment, the N-acetylneuraminic acid synthase (NeuB) is derived from *Neisseria meningitidis*.

In one embodiment, the N-acetylneuraminic acid synthase has an amino acid sequence set forth as SEQ ID NO:1.

In one embodiment, expression of the coding genes of the glucosamine-6-phosphate-N-acetyltransferase, the N-acetylglucosamine isomerase and the N-acetylneuraminic acid synthase in the recombinant *Bacillus subtilis* is enhanced through promoters.

In one embodiment, the glucosamine-6-phosphate-N-acetyltransferase has an amino acid sequence set forth as SEQ ID NO:3; and the N-acetylglucosamine isomerase has an amino acid sequence set forth as SEQ ID NO:5.

In one embodiment, the nucleotide sequences of the promoters are selected from SEQ ID NOs: 17-26.

In one embodiment, the recombinant *Bacillus subtilis* also expresses UDP-N-acetylglucosamine 2-epimerase (NeuC) and N-acetylglucosamine-6-phosphate-isomerase (NanE).

In one embodiment, the UDP-N-acetylglucosamine 2-epimerase has an amino acid sequence set forth as SEQ ID NO:9; and the N-acetylglucosamine-6-phosphate-isomerase has an amino acid sequence set forth as SEQ ID NO:11.

In one embodiment, the recombinant *Bacillus subtilis* also overexpresses glycerol kinase (GlpK); and the glycerol kinase has an amino acid sequence set forth as SEQ ID NO:7.

In one embodiment, the recombinant *Bacillus subtilis* overexpresses the glycerol kinase with a constitutive promoter set forth as SEQ ID NO:11.

In one embodiment, expression of the glucosamine-6-phosphate-N-acetyltransferase is enhanced with a promoter set forth as any one of SEQ ID NOs:17-19.

In one embodiment, expression of the N-acetylglucosamine isomerase is enhanced with a promoter set forth as any one of SEQ ID NOs:22-26.

In one embodiment, expression of the N-acetylglucosamine-6-phosphate-isomerase is enhanced with a promoter set forth as any one of SEQ ID NOs:17-19 or SEQ ID NOs:23-25.

In one embodiment, the recombinant *Bacillus subtilis* uses the promoter set forth as SEQ ID NO:17 to regulate the expression of the glucosamine-6-phosphate-N-acetyltransferase, uses the promoter set forth as SEQ ID NO: 18 to regulate the expression of the N-acetylglucosamine isomerase, and uses the promoter set forth as SEQ ID NO:17 to regulate the expression of the N-acetylneuraminic acid synthase.

In one embodiment, the recombinant *Bacillus subtilis* uses the promoter set forth as SEQ ID NO:17 to regulate the expression of glucosamine-6-phosphate-N-acetyltransferase, uses the promoter set forth as SEQ ID NO:26 to regulate the expression of N-acetylglucosamine isomerase, uses the promoter set forth as SEQ ID NO:17 to regulate the expression of N-acetylneuraminic acid synthase, uses the promoter set forth as SEQ ID NO:22 to regulate the expression of UDP-N-acetylglucosamine 2-epimerase, and uses the promoter set forth as SEQ ID NO:17 to regulate the expression of N-acetylglucosamine-6-phosphate-isomerase.

In one embodiment, the recombinant *Bacillus subtilis* uses the promoter set forth as SEQ ID NO:17 to regulate the expression of glucosamine-6-phosphate-N-acetyltransferase, uses the promoter set forth as SEQ ID NO:18 to regulate the expression of N-acetylglucosamine isomerase, uses the promoter set forth as SEQ ID NO:17 to regulate the expression of N-acetylneuraminic acid synthase, and uses the promoter set forth as SEQ ID NO:22 to regulate the expression of glycerol kinase.

In one embodiment, the *Bacillus subtilis* is *Bacillus subtilis* BSGN6-comK, and its construction method is disclosed in the paper Modular pathway engineering of key carbon-precursor supply-pathways for improved N-acetylneuraminic acid production in *Bacillus subtilis*.

The disclosure also provides a method for producing N-acetylneuraminic acid, including culturing any one of the above recombinant *Bacillus subtilis* in an environment containing sialic acid to produce the N-acetylneuraminic acid.

In one embodiment, the culturing process is performed at 30-37° C. for 16-72 h.

In one embodiment, the recombinant *Bacillus subtilis* is inoculated into an LB culture medium and cultured for 12-18 h to obtain a seed solution with an OD of 6-10, and then the seed solution is transferred to a fermentation culture medium at an inoculum concentration of 1-10% by volume for fermentation.

In one embodiment, the fermentation is performed in a culture medium containing glucose 60 g/L, tryptone 6 g/L, yeast powder 12 g/L, ammonium sulfate 6 g/L, dipotassium hydrogen phosphate 12.5 g/L, potassium dihydrogen phosphate 2.5 g/L, and magnesium sulfate 3 g/L.

The disclosure also provides a method for synthesizing N-acetylneuraminic acid. Glucose and glycerol are used as carbon sources and any one of the above *Bacillus subtilis* is used for fermentation.

In one embodiment, the content of the glucose is 40-80 g/L, and the content of the glycerol is 10-20 g/L.

In one embodiment, the *Bacillus subtilis* culture medium also contains tryptone, yeast powder, ammonium sulfate, dipotassium hydrogen phosphate, potassium dihydrogen phosphate, and magnesium sulfate.

In one embodiment, the recombinant *Bacillus subtilis* is inoculated into an LB culture medium and cultured for 12-18 h to obtain a seed solution, and then the seed solution is transferred to a fermentation culture medium at an inoculum concentration of 1-10% for fermentation.

In one embodiment, the *Bacillus subtilis* is fermented at 30-37° C. for 16-72 h.

The disclosure also claims to protect application of the recombinant *Bacillus subtilis* in preparation of N-acetylneuraminic acid or derivative products thereof.

In one embodiment, the application is for preparing medicines or health products.

In one embodiment, the derivative products include, but are not limited to, antiviral drugs Zanamivir or Oseltamivir.

Beneficial Effects (1) By screening N-acetylneuraminic acid synthase from different sources, the disclosure determines that the N-acetylneuraminic acid synthase derived from *Neisseria meningitidis* still has high catalytic activity at low expression levels, and integrates the N-acetylneuraminic acid synthase onto the recombinant *Bacillus subtilis* genome.

(2) The disclosure optimizes the expression levels of the key enzymes UDP-N-acetylglucosamine 2-epimerase (NeuC), N-acetylglucosamine-6-phosphate-isomerase (NanE), and glucosamine-6-phosphate-N-acetyltransferase (Gna1), N-acetylglucosamine isomerase (Age) and N-acetylneuraminic acid synthase (NeuB) of three N-acetylneuraminic acid synthesis pathways on the genome with 10 promoters of different strength, and reduces the expression level of the key enzyme NeuB, thereby reducing the protein synthesis pressure caused by the NeuB on the cell; and the N-acetylneuraminic acid production after fermentation of *Bacillus subtilis* for 72 h reaches 10.4 g/L, so the *Bacillus subtilis* has a good prospect for metabolic engineering applications.

(3) By overexpressing the glycerol kinase with a constitutive promoter P6, the disclosure enables *Bacillus subtilis* to use the artificial dual-carbon sources glucose and glycerol, thereby overcoming the carbon source metabolic decomposition repression effect in the presence of glucose, and improving the supply of intracellular phosphoenolpyruvic acid. Through rational regulation of the integrated expression of the glycerol kinase gene by the promoter, the N-acetylneuraminic acid production by the recombinant *Bacillus subtilis* is increased to 8.7 g/L.

BRIEF DESCRIPTION OF FIGURES

FIG. 1 is a diagram of the synthesis pathway of N-acetylneuraminic acid.

DETAILED DESCRIPTION

The N-acetylneuraminic acid synthase (NeuB) derived from *Neisseria meningitidis* has an amino acid sequence set forth as SEQ ID NO:1, and a nucleotide sequence set forth as SEQ ID NO:2.

The glucosamine-6-phosphate-N-acetyltransferase (Gna1) has an amino acid sequence set forth as SEQ ID NO:3, and a nucleotide sequence set forth as SEQ ID NO:4.

The N-acetylglucosamine isomerase (Age) has an amino acid sequence set forth as SEQ ID NO:5, and a nucleotide sequence set forth as SEQ ID NO:6.

The glycerol kinase (glpK) has an amino acid sequence set forth as SEQ ID NO:7, and a nucleotide sequence set forth as SEQ ID NO:8.

The UDP-N-acetylglucosamine 2-epimerase (NeuC) has an amino acid sequence set forth as SEQ ID NO:9, and a nucleotide sequence set forth as SEQ ID NO:10.

The N-acetylglucosamine-6-phosphate-isomerase (NanE) has an amino acid sequence set forth as SEQ ID NO:11, and a nucleotide sequence set forth as SEQ ID NO:12.

The NeuB derived from *E. coli* has an amino acid sequence set forth as SEQ ID NO: 13, and a nucleotide sequence set forth as SEQ ID NO: 14.

The NeuB derived from *Moritella viscosa* has an amino acid sequence set forth as SEQ ID NO: 15, and a nucleotide sequence set forth as SEQ ID NO: 16.

The nucleotide sequences of promoters P1-P10 are set forth as SEQ ID NOs:17-26 respectively.

The fermentation culture medium (g/L) contains: glucose 60, tryptone 6, yeast powder 12, ammonium sulfate 6, dipotassium hydrogen phosphate 12.5, potassium dihydrogen phosphate 2.5, and magnesium sulfate 3.

The two-carbon source fermentation culture medium (g/L) contains: tryptone 6, yeast powder 12, ammonium sulfate 6, dipotassium hydrogen phosphate 12.5, potassium dihydrogen phosphate 2.5, magnesium sulfate 3, glucose 60 g/L, and glycerol 20 g/L.

Detection method of N-acetylneuraminic acid: Agilent liquid chromatography is used for detection, the chromatographic column is Aminex HPX-87H column (300×7.8 mm), the absorption peak is detected by ultraviolet 210 nm, the mobile phase is 10 mM sulfuric acid, the flow rate is 0.5 mL/min, and the appearance time of N-acetylneuraminic acid is about 9.8 minutes.

Example 1 Construction of Genome Recombined and Integrated NemNeuB Fragment

Using the genome of *Bacillus subtilis* 168 as a template,

```
primers
NemNeuB-L-F:
                                    (SEQ ID NO: 27)
5'-CGGTGTCTGTATATCACAAAAATAGTGAGCAGGGTAACGA-3'
and NemNeuB-L-R:
                                    (SEQ ID NO: 28)
5'-CGCAATAACGCAGGCGTTCTGTGACATTAACTTATTTCCACCT

ATTTTGTTACAGCGTGTGCCACTTTTATGCA-3'
``` were designed, and a recombined and integrated NemNeuB left arm gene fragment was amplified.

The fragments of promoters P1-P10 set forth as SEQ ID NOs:17-26 were synthesized respectively.

The gene fragment encoding the N-acetylneuraminic acid synthase gene NeuB set forth as SEQ ID NO:2 was synthesized.

Using the genome of *Bacillus subtilis* 168 as a template, with

```
primers
NemNeuB-R-L:
                                    (SEQ ID NO: 29)
5'-TAACTTGTCAGACTGCCGGGAAATCCCGGCAGTCTTTTTTCCA

TTAAAACACGGCGCTTGAACAGCTTTTTTTGAATACCTTGTCCAGC

T-3'
and

NemNeuB-R-R:
                                    (SEQ ID NO: 30)
5'-GCGTCATCGCAGTTTTTGCACCTGACT-3',
``` a recombined and integrated NemNeuB right arm gene fragment was amplified.

The NemNeuB left arm gene fragment, the promoter fragments (set forth as SEQ ID NOs:17-26 respectively), the NemNeuB gene fragment and the NemNeuB right arm gene fragment were constructed by fusion PCR technology into recombined and integrated NemNeuB gene fragments, named NemNeuB-1 to NemNeuB-10 according to different promoters. NemNeuB-1 corresponds to the NemNeuB fusion fragment containing the promoter P1 set forth as SEQ ID NO:17, NemNeuB-2 corresponds to the NemNeuB fusion fragment containing the promoter P2 set forth as SEQ ID NO:18, and so on, NemNeuB-10 corresponds to the NemNeuB fusion fragment containing the promoter P10 set forth as SEQ ID NO:26.

Example 2 Construction of Genome Recombined and Integrated Gna1 Fragment

Using the genome of *Bacillus subtilis* 168 as a template,

```
primers
Gna1-L-F:
                                    (SEQ ID NO: 31)
5'-CGTGATATCGTCATTCAGTCTCTTGAACGCCA-3'
and Gna1-L-R:
                                    (SEQ ID NO: 32)
5'-CGCAATAACGCAGGCGTTCTGTGACATTAACTTATTTCATGTT

CTTTTTAGTTAGACGATTTTAATACAAGCCTCGCCA-3'
``` were designed, and a recombined and integrated Gna1 left arm gene fragment was amplified.

The fragments of promoters P1-P10 set forth as SEQ ID NOs:17-26 were synthesized.

The gene fragment encoding Gna1 set forth as SEQ ID NO:4 was synthesized.

Using the genome of *Bacillus subtilis* 168 as a template, with

```
primers
Gna1-R-L:
                                    (SEQ ID NO: 33)
5'-ATAACTTGTCAGACTGCCGGGAAATCCCGGCAGTCTTTTTTCC

ATTAAAACACGGCCCAGTCATAAAATAGTTTTCCTAATAAGACCTG

G-3'
and

Gna1-R-R:
                                    (SEQ ID NO: 34)
5'-CCTACTTAAGCTGCTACCACTTGTGA-3',
``` a recombined and integrated Gna1 right arm gene fragment was amplified.

The amplified Gna1 left arm gene fragment, the promoter fragments (set forth as SEQ ID NOs:17-26 respectively), the Gna1 gene fragment and the Gna1 right arm gene fragment were constructed by fusion PCR technology into recombined and integrated Gna1 gene fragments, named Gna1-1 to Gna1-10 according to different promoters. Gna1-1 corresponds to the Gna1 fusion fragment containing the promoter P1 set forth as SEQ ID NO:17, Gna1-2 corresponds to the Gna1 fusion fragment containing the promoter P2 set forth as SEQ ID NO:18, and so on, Gna1-10 corresponds to the Gna1 fusion fragment containing the promoter P10 set forth as SEQ ID NO:26.

Example 3 Construction of Genome Recombined and Integrated Age Fragment

Using the genome of *Bacillus subtilis* 168 as a template,

```
primers
Age-L-F:
                                    (SEQ ID NO: 35)
5'-CGTGATATCGTCATTCAGTCTCTTGAACGCCA-3'
and Age-L-R:
                                    (SEQ ID NO: 36)
5'-CGCAATAACGCAGGCGTTCTGTGACATTAACTTATTTCATGTT

CTTTTTAGTTAGACGATTTTAATACAAGCCTCGCCA-3'
``` were designed, and a recombined and integrated Age left arm gene fragment was amplified.

The fragments of promoters P1-P10 set forth as SEQ ID NOs:17-26 were synthesized.

The gene fragment encoding Age set forth as SEQ ID NO:6 was synthesized.

Using the genome of *Bacillus subtilis* as a template, with

```
primers
Age-R-L:
                                       (SEQ ID NO: 37)
5'-ATAACTTGTCAGACTGCCGGGAAATCCCGGCAGTCTTTTTCC

ATTAAAACACGGCCCAGTCATAAAATAGTTTTCCTAATAAGACCTG

G-3'
and

Age-R-R:
                                       (SEQ ID NO: 38)
5'-ATAACCAACGCAGCAAGTGGCAACCT-3',
``` a recombined and integrated Age right arm gene fragment was amplified.

The amplified Age left arm gene fragment, the promoter fragments (set forth as SEQ ID NOs:17-26 respectively), the Age gene fragment and the Age right arm gene fragment were constructed by fusion PCR technology into recombined and integrated Age gene fragments, named Age1 to Age10 according to different promoters. Age1 corresponds to the Age fusion fragment containing the promoter P1 set forth as SEQ ID NO:17, Age2 corresponds to the Age fusion fragment containing the promoter P2 set forth as SEQ ID NO:18, and so on, Age10 corresponds to the Age fusion fragment containing the promoter P10 set forth as SEQ ID NO:26.

Example 4 Construction of Genome Recombined and Integrated Glpk Fragment

Using the genome of *Bacillus subtilis* 168 as a template,

```
primers
glpK-L-F:
                                       (SEQ ID NO: 39)
5'-GTCGTACTGCCATCTGTTTCTGTATACATTCTCCCAAT-3'
and glpK-L-R:
                                       (SEQ ID NO: 40)
5'-CGCAATAACGCAGGCGTTCTGTGACATTAACTTATTTCTTTTT

ACCTTGTGATAAACAGGCACATGACGGCA-3'
``` were designed, and a recombined and integrated glpK left arm gene fragment was amplified.

The fragment of the promoter P6 set forth as SEQ ID NO:22 was synthesized. The gene fragment encoding glpK set forth as SEQ ID NO:8 was synthesized.

Using the genome of *Bacillus subtilis* 168 as a template, with

```
primers
glpK-R-L:
                                       (SEQ ID NO: 41)
5'-GAATAACTTGTCAGACTGCCGGGAAATCCCGGCAGTCTTTTTT

CCATTAAAACACGGCCCGCTGTCCTTGTTTTTTTCAGTCAATATTG

C-3'
and glpK-R-R:
                                       (SEQ ID NO: 42)
5'-GACATTTGCAGCGCCGGTTATCGCTCA-3',
``` a recombined and integrated glpK right arm gene fragment was amplified.

The glpk left arm gene fragment, the P6 promoter fragment (set forth as SEQ ID NO:22), the glpk gene fragment and the glpk right arm gene fragment were constructed by fusion PCR technology into a recombined and integrated glpK gene fragment, named glpK-6.

Example 5 Construction of Genome Recombined and Integrated NeuC Fragment

Using the genome of *Bacillus subtilis* 168 as a template,

```
primers
NeuC-L-F:
                                       (SEQ ID NO: 43)
5'-GCGAACAGGCATCCTATACACTGGGACAA-3'
and NeuC-L-R:
                                       (SEQ ID NO: 44)
5'-ACCGAGCTCGAATTCTTATTAGACGGAGTCTTTTTTGCTTTTG

CCAATCAGACGTGTAA-3'
``` were designed, and a recombined and integrated NeuC left arm gene fragment was amplified.

The fragments of promoters P1-P10 set forth as SEQ ID NOs:17-26 were synthesized.

The gene sequence of NeuC set forth as SEQ ID NO:10 was synthesized.

Using the genome of *Bacillus subtilis* 168 as a template, with

```
primers
NeuC-R-L:
                                       (SEQ ID NO: 45)
5'-ACTTGTCAGACTGCCGGGAAATCCCGGCAGTCTTTTTTCCATT

AAAACACGGCGACGGAGTCTTTTTTTATTTCGTTTTTAAGAAGTAG

G-3'
and

NeuC-R-R:
                                       (SEQ ID NO: 46)
5'-CTAACACAATCCATTTTGAAGATGCCTTTTTGCA-3',
``` a recombined and integrated NeuC right arm gene fragment was amplified.

The amplified NeuC left arm gene fragment, the promoter fragments (set forth as SEQ ID NOs:17-26 respectively), the NeuC gene fragment and the NeuC right arm gene fragment were constructed by fusion PCR technology into recombined and integrated NeuC gene fragments, named NeuC1 to NeuC10 according to different promoters. NeuC1 corresponds to the NeuC fusion fragment containing the promoter P1 set forth as SEQ ID NO:17, NeuC2 corresponds to the NeuC fusion fragment containing the promoter P2 set forth as SEQ ID NO:18, and so on, NeuC10 corresponds to the NeuC fusion fragment containing the promoter P10 set forth as SEQ ID NO:26.

Example 6 Construction of Genome Recombined and Integrated NanE Fragment

Using the genome of *Bacillus subtilis* 168 as a template,

```
primers
NanE-L-F:
                                    (SEQ ID NO: 47)
5'-GTGTTCGTAGTCTCTCGGGAGAGTCATTCCATGA-3'
and NanE-L-R:
                                    (SEQ ID NO: 48)
5'-CGCAATAACGCAGGCGTTCTGTGACATTAACTTATTTCGCGTT

TAAGAGAACAGGCCTTGGTTTGTGACA-3'
``` were designed, and a recombined and integrated NanE left arm gene fragment was amplified.

The fragments of promoters P1-P10 set forth as SEQ ID NOs:17-26 were synthesized.

The gene sequence of NanE set forth as SEQ ID NO:12 was synthesized.

Using the genome of *Bacillus subtilis* 168 as a template, with

```
primers
NanE-R-L:
                                    (SEQ ID NO: 49)
5'-GAATAACTTGTCAGACTGCCGGGAAATCCCGGCAGTCTTTTT CCATTAAAACACGGCATGACTGTCAGTTCTTTCAGCCGCT-3'
and NanE-R-R:
                                    (SEQ ID NO: 50)
5'-CAACGATTGCGTTTAATGTCAGCATCAGCCCATACA-3',
``` a recombined and integrated NanE right arm gene fragment was amplified.

The amplified NanE left arm gene fragment, the promoter fragments (set forth as SEQ ID NOs:17-26 respectively), the NanE gene fragment and the NanE right arm gene fragment were constructed by fusion PCR technology into recombined and integrated NanE gene fragments, named NanE1 to NanE10 according to different promoters. NanE1 corresponds to the NanE fusion fragment containing the promoter P1 set forth as SEQ ID NO:17, NanE2 corresponds to the NanE fusion fragment containing the promoter P2 set forth as SEQ ID NO:18, and so on, NanE10 corresponds to the NanE fusion fragment containing the promoter P10 set forth as SEQ ID NO:26.

Example 7 Construction of *Bacillus subtilis* BS-Gna1-1 to BS-Gna1-10 of Recombined and Integrated Gna1 Gene The recombined and integrated gene fragments of Gna1-1 to Gna1-10 constructed in Example 2 were transformed into the genome of *Bacillus subtilis* BSGN6-comK respectively (the construction method is disclosed in paper Modular pathway engineering of key carbon-precursor supply-pathways for improved N-acetylneuraminic acid production in *Bacillus subtilis*), and the obtained recombinant *Bacillus subtilis* was named BS-Gna1-1 to BS-Gna1-10 respectively.

The recombinant *Bacillus subtilis* BS-Gna1-1 to BS-Gna1-10 were inoculated into LB culture mediums respectively and cultured for 12-18 hours to obtain seed solutions with an OD of about 6. Then, the seed solutions were inoculated into fermentation culture mediums according to an inoculum concentration of 1%, and cultured at 37° C. and 200 rpm for 72 h. Finally, the production of the precursor substance N-acetylglucosamine (GlcNAc) of N-acetylneuraminic acid (NeuAc) detected in the fermentation broths was determined as: 8.4 g/L, 8.1 g/L, 8.1 g/L, 7.9 g/L, 7.8 g/L, 7.2 g/L, 7.8 g/L, 7.1 g/L, 7.2 g/L, and 7.2 g/L.

Example 8 Construction of *Bacillus subtilis* BS-Age-1 to BS-Age-10 of Recombined and Integrated Age Gene The recombined and integrated gene fragments of Age1 to Age10 constructed in Example 3 were transformed into the genome of the recombinant *Bacillus subtilis* BS-Gna1-1 constructed in Example 7 respectively, and the obtained recombinant *Bacillus subtilis* was named BSG-Age-1 to BSG-Age-10 respectively.

The recombinant *Bacillus subtilis* BSG-Age-1 to BSG-Age-10 were inoculated into LB culture mediums respectively and cultured for 12-18 hours to obtain seed solutions with an OD of about 6. Then, the seed solutions were inoculated into fermentation culture mediums according to an inoculum concentration of 1%, and cultured in the fermentation culture mediums at 37° C. and 200 rpm for 72 h. The production of the precursor substance N-acetyl-D-aminomannose (ManNAc) of N-acetylneuraminic acid (NeuAc) in the fermentation broths was determined as: 0.5 g/L, 0.4 g/L, 0.8 g/L, 1.4 g/L, 0.1 g/L, 2.8 g/L, 3.2 g/L, 2.9 g/L, 3.1 g/L, and 3.5 g/L.

Example 9 Construction of *Bacillus subtilis* of Recombined and Integrated NeuB Gene The recombined and integrated gene fragments of NeuB1 to NeuB10 constructed in Example 5 were transformed into the genome of the recombinant *Bacillus subtilis* BSG-Age-10 constructed in Example 7 respectively, and the obtained recombinant *Bacillus subtilis* was named BSGA-NeuB-1 to BSGA-NeuB-10 respectively.

The recombinant *Bacillus subtilis* BSGA-NeuB-1 to BSGA-NeuB-10 were inoculated into LB culture mediums respectively and cultured for 12-18 hours to obtain seed solutions with an OD of about 6. Then, the seed solutions were inoculated into fermentation culture mediums according to an inoculum concentration of 1%, and cultured in the fermentation culture mediums at 37° C. and 200 rpm for 72 h. The production of NeuAc in the fermentation broths was determined as: 7.6 g/L, 3.4 g/L, 3.1 g/L, 2.8 g/L, 3.7 g/L, 2.2 g/L, 1.9 g/L, 2.1 g/L, 1.7 g/L, and 1.9 g/L.

Example 10

(1) Construction of *Bacillus subtilis* of Recombined and Integrated Gna1 Gene

The recombined and integrated gene fragment of Gna1-1 constructed in Example 2 was transformed into the genome of *Bacillus subtilis* BSGN6-comK (the construction method is disclosed in paper Modular pathway engineering of key carbon-precursor supply-pathways for improved N-acetylneuraminic acid production in *Bacillus subtilis*), and the obtained recombinant *Bacillus subtilis* engineering strain was named BS-Gna1.

(2) Construction of *Bacillus subtilis* of Recombined and Integrated Age Gene

The recombined and integrated gene fragment of Age-2 constructed in Example 3 was transformed into the genome of the recombinant *Bacillus subtilis* BS-Gna1 constructed in step (1), and the obtained recombinant *Bacillus subtilis* engineering strain was named BSG-Age-2.

(3) Construction of *Bacillus subtilis* of Recombined and Integrated NemNeuB Gene The recombined and integrated gene fragment of NemNeuB-1 constructed in Example 1 was transformed into the genome of the recombinant *Bacillus subtilis* BSG-Age-2 constructed in step (2), and the obtained recombinant *Bacillus subtilis* engineering strain was named BSGA-Nem-NeuB-1.

(4) Construction of *Bacillus subtilis* of Recombined and Integrated P6-glpK Gene The recombined and integrated gene fragment of glpk-6 constructed in Example 4 was transformed into the genome of the recombinant *Bacillus subtilis* BSGA-NemNeuB-1 constructed in step (3), and the obtained recombinant *Bacillus subtilis* was named BSGAN-glpk-6.

The recombinant *Bacillus subtilis* BSGAN-glpk-6 was inoculated into an LB culture medium and cultured for 12-18 hours to obtain a seed solution with an OD of about 6. Then the seed solution was inoculated into a fermentation culture medium according to an inoculum concentration of 1% by volume, and cultured at 37° C. and 200 rpm for 72 h. The NeuAc production in the fermentation broth was determined as 8.7 g/L.

Comparative Example 1: Synthesis of NeuAc by Strengthening the Age-NeuB Pathway Only The same strategy as in Example 3 was adopted, and the difference is that the promoter fragment was not fused. The specific operation flow is: Using the genome of *Bacillus subtilis* 168 as a template, recombined and integrated Age left arm gene fragment and Age right arm gene fragment were amplified, and a gene fragment encoding Age set forth as SEQ ID NO:19 was synthesized. The amplified Age left arm gene fragment, the Age gene fragment and the Age right arm fragment were constructed by fusion PCR technology into a recombined and integrated Age gene fragment. Then the recombined and integrated Age gene fragment was transformed into the genome of the recombinant *Bacillus subtilis* BS-Gna1-1 according to the method of Example 8 to obtain recombinant *Bacillus subtilis* BSG-Age.

The same strategy as in Example 1 was adopted, and the difference is that the promoter fragment was not fused. The specific operation flow is: Using the genome of *Bacillus subtilis* 168 as a template, a recombined and integrated NemNeuB left arm gene fragment and a recombined and integrated NemNeuB right arm gene fragment were amplified. A gene fragment encoding the N-acetylneuraminic acid synthase gene set forth as SEQ ID NO:2 was synthesized. The NemNeuB left arm gene fragment, the NemNeuB gene fragment and the NemNeuB right arm gene fragment were constructed by fusion PCR technology into a recombined and integrated NemNeuB gene fragment. Then the recombined and integrated NemNeuB gene fragment was transformed into the recombinant *Bacillus subtilis* BSG-Age to obtain recombinant *Bacillus subtilis* BSGA-NeuB.

The recombinant *Bacillus subtilis* BSGA-NeuB was cultured at 37° C. and 200 rpm in a fermentation culture medium for 72 h, and the maximum production of NeuAc can only reach 2.75 g/L.

Comparative Example 2: Effect of N-Acetylneuraminic Acid Synthase from Different Sources on Expression Effect With the same strategy as in Example 5, NeuB genes derived from *E. coli* K1, *Moritella viscosa*, and the like were expressed in *Bacillus subtilis* BSGN6-comK, and different promoters were used to regulate expression. Under the same culture conditions as in Example 9, the N-acetylneuraminic acid production after fermentation for 16-72 h is shown in Table 1.

TABLE 1

N-acetylneuraminic acid production of recombinant *Bacillus subtilis* expressing NeuB derived from different sources

| Source | Promoter sequence | Amino acid sequence | Nucleotide sequence | Production (g/L) |
|---|---|---|---|---|
| *E. coli* K1 | SEQ ID NO: 17 | SEQ ID NO: 13 | SEQ ID NO: 14 | 0.1 g/L |
| | SEQ ID NO: 18 | | | 0.1 g/L |
| | SEQ ID NO: 19 | | | 0.1 g/L |
| | SEQ ID NO: 20 | | | 0.1 g/L |
| | SEQ ID NO: 21 | | | 0.3 g/L |
| | SEQ ID NO: 22 | | | 2.2 g/L |
| | SEQ ID NO: 23 | | | 4.5 g/L |
| | SEQ ID NO: 24 | | | 4.1 g/L |
| | SEQ ID NO: 25 | | | 3.5 g/L |
| | SEQ ID NO: 26 | | | 3.3 g/L |
| *Moritella viscosa* | SEQ ID NO: 17 | SEQ ID NO: 15 | SEQ ID NO: 16 | 0.1 g/L |
| | SEQ ID NO: 18 | | | 0.1 g/L |
| | SEQ ID NO: 19 | | | 0.1 g/L |
| | SEQ ID NO: 20 | | | 0.5 g/L |
| | SEQ ID NO: 21 | | | 1.1 g/L |
| | SEQ ID NO: 22 | | | 1.6 g/L |
| | SEQ ID NO: 23 | | | 1.9 g/L |
| | SEQ ID NO: 24 | | | 2.5 g/L |
| | SEQ ID NO: 25 | | | 2.2 g/L |
| | SEQ ID NO: 26 | | | 2.0 g/L |

Comparative Example 3: Production of NeuAc by Recombinant *Bacillus subtilis* without P6-glpK Integration The recombinant *Bacillus subtilis* BSGA-NemNeuB-1 prepared according to the method of Example 8 was inoculated into an LB culture medium and cultured for 12-18 hours to obtain a seed solution with an OD of about 6. Then, the seed solution was inoculated into a fermentation culture medium at an inoculum concentration of 1% by volume, and cultured at 37° C. and 200 rpm for 72 h. The NeuAc production in the fermentation broth was determined as 7.6 g/L.

Comparative Example 4 Production of NeuAc by Recombinant *Bacillus subtilis* with GlpK Fused with Different Promoters The same strategy as in Example 8 was adopted, and the difference is that the promoters are replaced with the promoter P1 of SEQ ID NO:17, the promoter P2 of SEQ ID NO:18, and the promoter P3 of SEQ ID NO:19, respectively. The recombinant integrated glpk fragment was constructed, and the recombinant integrated glpk fragment was transformed into the genome of *Bacillus subtilis* BSGA-NemNeuB-1. Fermentation was performed under the same conditions. The results show that the production of N-acetylneuraminic acid after the same fermentation time was 7.4 g/L, 7.2 g/L and 7.5 g/L respectively, which are lower than the production of the disclosure of 8.7 g/L.

TABLE 2

Effect of glpk strengthened by different promoters on production of N-acetylneuraminic acid

| Recombinant strain name | Nucleotide sequence of promoter | Production (g/L) |
|---|---|---|
| BSGAN-glpk-1 | SEQ ID NO: 9 | 7.4 |
| BSGAN-glpk-2 | SEQ ID NO: 12 | 7.2 |
| BSGAN-glpk-3 | SEQ ID NO: 13 | 7.5 |

Although the disclosure has been disclosed as above in preferred examples, it is not intended to limit the disclosure.

Anyone familiar with the technology can make various changes and modifications without departing from the spirit and scope of the disclosure. Therefore, the protection scope of the disclosure should be defined by the claims.

What is claimed is:

1. Recombinant *Bacillus subtilis*, expressing glucosamine-6-phosphate-N-acetyltransferase, N-acetylglucosamine isomerase and N-acetylneuraminic acid synthase (NeuB), wherein the N-acetylneuraminic acid synthase (NeuB) is derived from *Neisseria meningitidis*; wherein the N-acetylneuraminic acid synthase has an amino acid sequence set forth as SEQ ID NO:1; wherein expression of coding genes of the glucosamine-6-phosphate-N-acetyltransferase, the N-acetylglucosamine isomerase and the N-acetylneuraminic acid synthase in the recombinant *Bacillus subtilis* is enhanced by promoters; and nucleotide sequences of the promoters are selected from SEQ ID NOs:17-26; wherein the glucosamine-6-phosphate-N-acetyltransferase has an amino acid sequence set forth as SEQ ID NO:3; and the N-acetylglucosamine isomerase has an amino acid sequence set forth as SEQ ID NO:5; wherein the recombinant *Bacillus subtilis* also expresses UDP-N-acetylglucosamine 2-epimerase (NeuC) and N-acetylglucosamine-6-phosphate-isomerase (NanE).

2. The recombinant *Bacillus subtilis* of claim 1, wherein the UDP-N-acetylglucosamine 2-epimerase has an amino acid sequence set forth as SEQ ID NO:9; and the N-acetyl-glucosamine-6-phosphate-isomerase has an amino acid sequence set forth as SEQ ID NO:11.

3. The recombinant *Bacillus subtilis* of claim 1, wherein the recombinant *Bacillus subtilis* also overexpresses glycerol kinase (GlpK); and the glycerol kinase has an amino acid sequence set forth as SEQ ID NO:7.

4. The recombinant *Bacillus subtilis* of claim 3, wherein the recombinant *Bacillus subtilis* overexpresses the glycerol kinase with a constitutive promoter set forth as SEQ ID NO:11.

5. The recombinant *Bacillus subtilis* of claim 1, wherein the recombinant *Bacillus subtilis* uses the promoter set forth as SEQ ID NO:17 to regulate the expression of the glucosamine-6-phosphate-N-acetyltransferase, uses the promoter set forth as SEQ ID NO: 18 to regulate the expression of the N-acetylglucosamine isomerase, and uses the promoter set forth as SEQ ID NO:17 to regulate the expression of the N-acetylneuraminic acid synthase.

6. The recombinant *Bacillus subtilis* of claim 1, wherein the recombinant *Bacillus subtilis* uses the promoter set forth as SEQ ID NO:17 to regulate the expression of glucosamine-6-phosphate-N-acetyltransferase, uses the promoter set forth as SEQ ID NO:26 to regulate the expression of N-acetylglucosamine isomerase, uses the promoter set forth as SEQ ID NO:17 to regulate the expression of N-acetylneuraminic acid synthase, uses the promoter set forth as SEQ ID NO:22 to regulate the expression of UDP-N-acetylglucosamine 2-epimerase, and uses the promoter set forth as SEQ ID NO:17 to regulate the expression of N-acetylglucosamine-6-phosphate-isomerase.

7. The recombinant *Bacillus subtilis* of claim 1, wherein the recombinant *Bacillus subtilis* uses the promoter set forth as SEQ ID NO:17 to regulate the expression of glucosamine-6-phosphate-N-acetyltransferase, uses the promoter set forth as SEQ ID NO:18 to regulate the expression of N-acetylglucosamine isomerase, uses the promoter set forth as SEQ ID NO:17 to regulate the expression of N-acetylneuraminic acid synthase, and uses the promoter set forth as SEQ ID NO:22 to regulate the expression of glycerol kinase.

8. A method for producing N-acetylneuraminic acid, comprising culturing the recombinant *Bacillus subtilis* of claim 1 in an environment containing sialic acid to produce the N-acetylneuraminic acid.

9. The method of claim 8, wherein the culturing is performed at 30-37° C. for 16-72 h.

10. A method for synthesizing N-acetylneuraminic acid, comprising using glucose and glycerol as carbon sources and using the *Bacillus subtilis* of claim 3 to perform fermentation.

11. The method of claim 10, wherein a content of the glucose is 40-80 g/L, and a content of the glycerol is 10-20 g/L.

* * * * *

```
                          SEQUENCE LISTING

<160> NUMBER OF SEQ ID NOS: 50

<210> SEQ ID NO 1
<211> LENGTH: 349
<212> TYPE: PRT
<213> ORGANISM: Neisseria meningitidis

<400> SEQUENCE: 1

Met Gln Asn Asn Asn Glu Phe Lys Ile Gly Asn Arg Ser Val Gly Tyr
1               5                   10                  15

Asn His Glu Pro Leu Ile Ile Cys Glu Ile Gly Ile Asn His Glu Gly
            20                  25                  30

Ser Leu Lys Thr Ala Phe Glu Met Val Asp Ala Ala Tyr Asn Ala Gly
        35                  40                  45

Ala Glu Val Val Lys His Gln Thr His Ile Val Glu Asp Glu Met Ser
    50                  55                  60

Asp Glu Ala Lys Gln Val Ile Pro Gly Asn Ala Asp Val Ser Ile Tyr
65                  70                  75                  80

Glu Ile Met Glu Arg Cys Ala Leu Asn Glu Glu Asp Glu Ile Lys Leu
                85                  90                  95

Lys Glu Tyr Val Glu Ser Lys Gly Met Ile Phe Ile Ser Thr Pro Phe
            100                 105                 110

Ser Arg Ala Ala Ala Leu Arg Leu Gln Arg Met Asp Ile Pro Ala Tyr
        115                 120                 125

Lys Ile Gly Ser Gly Glu Cys Asn Asn Tyr Pro Leu Ile Lys Leu Val
    130                 135                 140

Ala Ser Phe Gly Lys Pro Ile Ile Leu Ser Thr Gly Met Asn Ser Ile
145                 150                 155                 160

Glu Ser Ile Lys Lys Ser Val Glu Ile Ile Arg Glu Ala Gly Val Pro
                165                 170                 175

Tyr Ala Leu Leu His Cys Thr Asn Ile Tyr Pro Thr Pro Tyr Glu Asp
            180                 185                 190

Val Arg Leu Gly Gly Met Asn Asp Leu Ser Glu Ala Phe Pro Asp Ala
        195                 200                 205

Ile Ile Gly Leu Ser Asp His Thr Leu Asp Asn Tyr Ala Cys Leu Gly
    210                 215                 220

Ala Val Ala Leu Gly Gly Ser Ile Leu Glu Arg His Phe Thr Asp Arg
225                 230                 235                 240

Met Asp Arg Pro Gly Pro Asp Ile Val Cys Ser Met Asn Pro Asp Thr
                245                 250                 255

Phe Lys Glu Leu Lys Gln Gly Ala His Ala Leu Lys Leu Ala Arg Gly
            260                 265                 270

Gly Lys Lys Asp Thr Ile Ile Ala Gly Glu Lys Pro Thr Lys Asp Phe
        275                 280                 285

Ala Phe Ala Ser Val Val Ala Asp Lys Asp Ile Lys Lys Gly Glu Leu
    290                 295                 300

Leu Ser Gly Asp Asn Leu Trp Val Lys Arg Pro Gly Asn Gly Asp Phe
305                 310                 315                 320

Ser Val Asn Glu Tyr Glu Thr Leu Phe Gly Lys Val Ala Ala Cys Asn
                325                 330                 335

Ile Arg Lys Gly Ala Gln Ile Lys Lys Thr Asp Ile Glu
            340                 345
```

<210> SEQ ID NO 2
<211> LENGTH: 1050
<212> TYPE: DNA
<213> ORGANISM: Neisseria meningitidis

<400> SEQUENCE: 2

```
atgcaaaaca acaacgaatt taaaatcggc aacagatcag tcggatataa tcatgaaccg    60
cttattatct gcgaaattgg catcaaccat gaaggaagct taaaaacagc ctttgaaatg   120
gtcgatgcag cgtataatgc cggagcagaa gttgtgaaac atcaaacaca tatcgttgaa   180
gatgaaatgt ctgatgaagc caaacaggtg atcccgggca acgcagatgt ctcaatctac   240
gaaatcatgg aaagatgtgc gctgaacgaa gaagatgaaa tcaaactgaa agaatacgtt   300
gaaagcaaag gaatgatctt tatctctaca ccgttttcac gcgctgccgc acttagatta   360
cagcgcatgg atattccggc ctataaaatc ggctctggag aatgcaacaa ctacccgctg   420
atcaaactgg tggcaagctt tggcaaaccg atcatcctgt ctacaggaat gaactcaatc   480
gaaagcatca aaaaatcagt tgaaatcatc agagaagcgg gcgtgccgta tgctctgctt   540
cattgtacaa acatttatcc gacaccgtat gaagatgttc gcctgggcgg aatgaatgat   600
ctttcagaag ccttttccgga tgcaattatc ggccttagcg atcatacatt agataactat   660
gcatgcctgg gagcggtggc tcttggcgga tctatcctgg aaagacattt tacagataga   720
atggatcgcc cgggcccgga tatcgtctgt tcaatgaatc cggatacatt taagaactg    780
aaacaaggag cccatgcact gaaacttgcg agaggcggca agaaagatac aattatcgct   840
ggcgaaaaac cgacaaaaga ttttgcgttt gctagcgtcg ttgcggataa agatattaag   900
aaaggcgaac tgctgtctgg agataacctg tgggtcaaaa gaccgggcaa cggagatttt   960
agcgttaacg aatacgaaac acttttggc aaagtggcgg cttgcaatat ccgcaaagga  1020
gctcagatta agaaaacaga tatcgaataa                                    1050
```

<210> SEQ ID NO 3
<211> LENGTH: 165
<212> TYPE: PRT
<213> ORGANISM: Artificial Sequence
<220> FEATURE:
<223> OTHER INFORMATION: Protein translated from synthetic DNA

<400> SEQUENCE: 3

```
Met Ser His Ile Phe Asp Ala Ser Val Leu Ala Pro His Ile Pro Ser
1               5                   10                  15

Asn Leu Pro Asp Asn Phe Lys Val Arg Pro Leu Ala Lys Asp Asp Phe
            20                  25                  30

Ser Lys Gly Tyr Val Asp Leu Leu Ser Gln Leu Thr Ser Val Gly Asn
        35                  40                  45

Leu Asp Gln Glu Ala Phe Glu Lys Arg Phe Glu Ala Met Arg Thr Ser
    50                  55                  60

Val Pro Asn Tyr His Ile Val Val Ile Glu Asp Ser Asn Ser Gln Lys
65                  70                  75                  80

Val Val Ala Ser Ala Ser Leu Val Val Glu Met Lys Phe Ile His Gly
                85                  90                  95

Ala Gly Ser Arg Gly Arg Val Glu Asp Val Val Asp Thr Glu Met
            100                 105                 110

Arg Arg Gln Lys Leu Gly Ala Val Leu Leu Lys Thr Leu Val Ser Leu
        115                 120                 125

Gly Lys Ser Leu Gly Val Tyr Lys Ile Ser Leu Glu Cys Val Pro Glu
```

```
                130                 135                 140
Leu Leu Pro Phe Tyr Ser Gln Phe Gly Phe Gln Asp Asp Cys Asn Phe
145                 150                 155                 160

Met Thr Gln Arg Phe
                165
```

<210> SEQ ID NO 4
<211> LENGTH: 498
<212> TYPE: DNA
<213> ORGANISM: Artificial Sequence
<220> FEATURE:
<223> OTHER INFORMATION: Synthetic DNA

<400> SEQUENCE: 4

```
atgagccata tcttcgacgc atctgtactg gctccacata ttcctagtaa ccttcctgat    60
aatttcaagg tgagaccact ggcaaaggat gattttcga agggatatgt cgacctgctg   120
tcacaattga cgtcagttgg aaaccttgac caagaagcat ttgagaaacg atttgaggcg   180
atgagaacaa gcgtaccgaa ttatcacatc gtagtaattg aggattccaa cagccagaaa   240
gtggtggcgt ctgctagttt ggttgttgaa atgaaattca ttcatggggc cggatcaagg   300
ggtcgtgttg aagatgttgt cgtcgataca gaaatgcgcc ggcaaaaatt aggtgccgtg   360
cttttaaaaa ctttggtgtc acttggcaaa tctttaggcg tctacaaaat aagcctcgaa   420
tgcgtcccgg aattactccc gttctattcc caatttggct ttcaggatga ctgtaatttt   480
atgacccagc gcttttaa                                                 498
```

<210> SEQ ID NO 5
<211> LENGTH: 388
<212> TYPE: PRT
<213> ORGANISM: Artificial Sequence
<220> FEATURE:
<223> OTHER INFORMATION: Protein translated from synthetic DNA

<400> SEQUENCE: 5

```
Met Gly Lys Asn Leu Gln Ala Leu Ala Gln Leu Tyr Lys Asn Ala Leu
1               5                   10                  15

Leu Asn Asp Val Leu Pro Phe Trp Glu Asn His Ser Leu Asp Ser Glu
                20                  25                  30

Gly Gly Tyr Phe Thr Cys Leu Asp Arg Gln Gly Lys Val Tyr Asp Thr
            35                  40                  45

Asp Lys Phe Ile Trp Leu Gln Asn Arg Gln Val Trp Thr Phe Ser Met
        50                  55                  60

Leu Cys Asn Gln Leu Glu Lys Arg Glu Asn Trp Leu Lys Ile Ala Arg
65                  70                  75                  80

Asn Gly Ala Lys Phe Leu Ala Gln His Gly Arg Asp Asp Glu Gly Asn
                85                  90                  95

Trp Tyr Phe Ala Leu Thr Arg Gly Gly Glu Pro Leu Val Gln Pro Tyr
            100                 105                 110

Asn Ile Phe Ser Asp Cys Phe Ala Ala Met Ala Phe Ser Gln Tyr Ala
        115                 120                 125

Leu Ala Ser Gly Glu Glu Trp Ala Lys Asp Val Ala Met Gln Ala Tyr
    130                 135                 140

Asn Asn Val Leu Arg Arg Lys Asp Asn Pro Lys Gly Lys Tyr Thr Lys
145                 150                 155                 160

Thr Tyr Pro Gly Thr Arg Pro Met Lys Ala Leu Ala Val Pro Met Ile
                165                 170                 175
```

```
Leu Ala Asn Leu Thr Leu Glu Met Glu Trp Leu Pro Gln Thr
            180                 185                 190

Leu Glu Asn Val Leu Ala Ala Thr Val Gln Glu Val Met Gly Asp Phe
        195                 200                 205

Leu Asp Gln Glu Gln Gly Leu Met Tyr Glu Asn Val Ala Pro Asp Gly
    210                 215                 220

Ser His Ile Asp Cys Phe Gly Arg Leu Ile Asn Pro Gly His Gly
225                 230                 235                 240

Ile Glu Ala Met Trp Phe Ile Met Asp Ile Ala Arg Arg Lys Asn Asp
                245                 250                 255

Ser Lys Thr Ile Asn Gln Ala Val Asp Val Val Leu Asn Ile Leu Asn
            260                 265                 270

Phe Ala Trp Asp Asn Glu Tyr Gly Gly Leu Tyr Tyr Phe Met Asp Ala
        275                 280                 285

Ala Gly His Pro Pro Gln Gln Leu Glu Trp Asp Gln Lys Leu Trp Trp
    290                 295                 300

Val His Leu Glu Ser Leu Val Ala Leu Ala Met Gly Tyr Arg Leu Thr
305                 310                 315                 320

Gly Arg Asp Ala Cys Trp Ala Trp Tyr Gln Lys Met His Asp Tyr Ser
                325                 330                 335

Trp Gln His Phe Ala Asp Pro Glu Tyr Gly Glu Trp Phe Gly Tyr Leu
            340                 345                 350

Asn Arg Arg Gly Glu Val Leu Leu Asn Leu Lys Gly Lys Trp Lys
        355                 360                 365

Gly Cys Phe His Val Pro Arg Ala Met Tyr Leu Cys Trp Gln Gln Phe
    370                 375                 380

Glu Ala Leu Ser
385

<210> SEQ ID NO 6
<211> LENGTH: 1167
<212> TYPE: DNA
<213> ORGANISM: Artificial Sequence
<220> FEATURE:
<223> OTHER INFORMATION: Synthetic DNA

<400> SEQUENCE: 6
atgggcaaaa acttacaagc tctggcccag ctttataaaa atgccctgct taacgatgtg      60
cttccgtttt gggaaaatca ttcattagat agcgaaggcg atattttac atgcctggat      120 agacagggca agtctacga tacagataaa tttatctggc ttcaaaaccg ccaggtttgg      180
acattttcta tgctttgtaa ccagctggaa aaagagaaa actggctgaa aatcgctcgc      240
aatggagcca aatttctggc acaacatggc agagatgatg aaggaaactg gtattttgct      300
ttaacacgcg gcggagaacc gctggttcaa ccgtataata ttttttagcga ttgctttgca      360 gcgatggcct ttctcagta tgcattagcg tcaggagaag aatgggcaaa agatgttgct      420
atgcaagcct ataataacgt gctgagacgc aaagataacc cgaaaggcaa atacacaaaa      480
acatatccgg gaacaagacc gatgaaagct ttagccgttc cgatgattct ggcgaacctg      540
acacttgaaa tggaatggtt actgccgcaa gaaacactgg aaaatgtgct tgctgccaca      600
gtccaggaag ttatgggcga ttttcttgat caagaacagg gattaatgta tgaaaacgtc      660
gctccggatg gctcacatat cgattgcttt gaaggacgcc tgattaatcc gggccatgga      720
atcgaagcga tgtggtttat tatggatatc gctagacgca aaaacgatag caaaacaatc      780
aaccaggcgg ttgatgttgt gttaaatatc ctgaactttg cttgggataa cgaatacggc      840
```

```
ggactttact actttatgga tgcagcgggc catccgccgc aacagctgga atgggatcaa      900
aaactttggt gggtgcatct tgaaagctta gtcgcactgg cgatgggcta tagattaaca      960
ggacgcgatg catgttgggc gtggtatcaa aaaatgcatg attattcttg gcagcatttt     1020
gcagatccgg aatatggcga atggtttgga tatcttaaca gacgcggcga agtgcttctg     1080
aacctgaaag gcggaaaatg gaaaggatgc tttcatgtcc cgagagccat gtatctgtgt     1140
tggcaacagt ttgaagcact ttcataa                                         1167
```

<210> SEQ ID NO 7
<211> LENGTH: 496
<212> TYPE: PRT
<213> ORGANISM: Artificial Sequence
<220> FEATURE:
<223> OTHER INFORMATION: Protein translated from synthetic DNA

<400> SEQUENCE: 7

```
Met Glu Thr Tyr Ile Leu Ser Leu Asp Gln Gly Thr Thr Ser Ser Arg
1               5                   10                  15

Ala Ile Leu Phe Asn Lys Glu Gly Lys Ile Val His Ser Ala Gln Lys
            20                  25                  30

Glu Phe Thr Gln Tyr Phe Pro His Pro Gly Trp Val Glu His Asn Ala
        35                  40                  45

Asn Glu Ile Trp Gly Ser Val Leu Ala Val Ile Ala Ser Val Ile Ser
    50                  55                  60

Glu Ser Gly Ile Ser Ala Ser Gln Ile Ala Gly Ile Gly Ile Thr Asn
65                  70                  75                  80

Gln Arg Glu Thr Thr Val Val Trp Asp Lys Asp Thr Gly Ser Pro Val
                85                  90                  95

Tyr Asn Ala Ile Val Trp Gln Ser Arg Gln Thr Ser Gly Ile Cys Glu
            100                 105                 110

Glu Leu Arg Glu Lys Gly Tyr Asn Asp Lys Phe Arg Glu Lys Thr Gly
        115                 120                 125

Leu Leu Ile Asp Pro Tyr Phe Ser Gly Thr Lys Val Lys Trp Ile Leu
    130                 135                 140

Asp Asn Val Glu Gly Ala Arg Glu Lys Ala Glu Lys Gly Glu Leu Leu
145                 150                 155                 160

Phe Gly Thr Ile Asp Thr Trp Leu Ile Trp Lys Met Ser Gly Gly Lys
                165                 170                 175

Ala His Val Thr Asp Tyr Ser Asn Ala Ser Arg Thr Leu Met Phe Asn
            180                 185                 190

Ile Tyr Asp Leu Lys Trp Asp Asp Glu Leu Leu Asp Ile Leu Gly Val
        195                 200                 205

Pro Lys Ser Met Leu Pro Glu Val Lys Pro Ser Ser His Val Tyr Ala
    210                 215                 220

Glu Thr Val Asp Tyr Arg Phe Phe Gly Lys Asn Ile Pro Ile Ala Gly
225                 230                 235                 240

Ala Ala Gly Asp Gln Gln Ser Ala Leu Phe Gly Gln Ala Cys Phe Glu
                245                 250                 255

Glu Gly Met Gly Lys Asn Thr Tyr Gly Thr Gly Cys Phe Met Leu Met
            260                 265                 270

Asn Thr Gly Glu Lys Ala Ile Lys Ser Glu His Gly Leu Leu Thr Thr
        275                 280                 285

Ile Ala Trp Gly Ile Asp Gly Lys Val Asn Tyr Ala Leu Glu Gly Ser
    290                 295                 300
```

```
Ile Phe Val Ala Gly Ser Ala Ile Gln Trp Leu Arg Asp Gly Leu Arg
305                 310                 315                 320

Met Phe Gln Asp Ser Ser Leu Ser Glu Ser Tyr Ala Glu Lys Val Asp
            325                 330                 335

Ser Thr Asp Gly Val Tyr Val Val Pro Ala Phe Val Gly Leu Gly Thr
        340                 345                 350

Pro Tyr Trp Asp Ser Asp Val Arg Gly Ser Val Phe Gly Leu Thr Arg
    355                 360                 365

Gly Thr Thr Lys Glu His Phe Ile Arg Ala Thr Leu Glu Ser Leu Ala
370                 375                 380

Tyr Gln Thr Lys Asp Val Leu Asp Ala Met Glu Ala Asp Ser Asn Ile
385                 390                 395                 400

Ser Leu Lys Thr Leu Arg Val Asp Gly Gly Ala Val Lys Asn Asn Phe
            405                 410                 415

Leu Met Gln Phe Gln Gly Asp Leu Leu Asn Val Pro Val Glu Arg Pro
        420                 425                 430

Glu Ile Asn Glu Thr Thr Ala Leu Gly Ala Ala Tyr Leu Ala Gly Ile
    435                 440                 445

Ala Val Gly Phe Trp Lys Asp Arg Ser Glu Ile Ala Asn Gln Trp Asn
450                 455                 460

Leu Asp Lys Arg Phe Glu Pro Glu Leu Glu Glu Lys Arg Asn Glu
465                 470                 475                 480

Leu Tyr Lys Gly Trp Gln Lys Ala Val Lys Ala Ala Met Ala Phe Lys
            485                 490                 495
```

<210> SEQ ID NO 8
<211> LENGTH: 1491
<212> TYPE: DNA
<213> ORGANISM: Artificial Sequence
<220> FEATURE:
<223> OTHER INFORMATION: Synthetic DNA

<400> SEQUENCE: 8

```
atggaaacgt acattttatc cttagatcag gggacgacaa gttcaagagc gattctgttt      60
aataaagaag gcaaaattgt ccactctgct caaaaggaat ttacacaata cttcccgcat     120
cctggctggg ttgagcataa tgccaatgaa atttggggct ctgtcctcgc ggttatcgcc     180
tcagtcatct ctgaatcagg aatcagcgct tctcaaattg ccggcatcgg catcacgaac     240
cagcgcgaga cgacggttgt gtgggataaa gatacaggaa gtcctgtcta atgcaatc      300
gtttggcagt ccagacagac gtccggcatt tgtgaggaac ttcgtgaaaa aggatataat     360
gataaattca gagaaaaaac agggcttttta atcgatcctt acttctccgg cacgaaggtg    420
aagtggattt tagacaatgt ggaaggcgca agagaaaaag cggaaaaagg cgagctgctg     480
tttggaacga ttgatacgtg gctcatttgg aaaatgtcag gcggaaaagc gcatgtgacc     540
gattactcca tgcctcaag aacactgatg tttaatattt acgatttaaa atgggacgat     600
gaactgctcg acattctagg cgtaccgaaa tccatgctcc ctgaagtgaa gccgtcctct     660
catgtgtatg cggagactgt tgattatagg ttcttcggaa aaaatatccc gattgctgga     720
gcggcaggcg accagcagtc cgcattgttc ggccaggcat gctttgaaga aggcatgggg     780
aaaaacactt acggcacagg atgtttcatg ctgatgaata ccggggaaaa agcaattaag     840
tccgaacatg gcttttgac aacaatcgct tggggcattg acggaaaagt gaactatgcg     900
ttagaaggga gcatttttgt cgcaggctct gccatccagt ggcttagaga cggtttgaga     960
```

```
atgttccagg attcatcgct aagcgaatct tatgcagaaa aagtggattc aactgacggc    1020
gtgtatgttg ttccagcatt tgtcggactg ggaacgcctt actgggacag cgatgtgcgc    1080
ggttcggttt tcggcctgac aagagggaca acaaaagagc actttatccg tgcgacactg    1140
gagtcattgg cttatcagac caaagatgtg cttgacgcaa tggaagcaga ttcaaacatt    1200
tcattaaaga cgctccgtgt agacggagga gctgtaaaaa acaatttcct aatgcagttc    1260
caaggagacc tgttgaatgt tcctgtggag cgcccggaaa ttaatgaaac gactgcactt    1320
ggcgcggctt atttggcggg tatcgctgtg ggattctgga aggaccgttc tgaaatcgcg    1380
aaccagtgga atctggataa acggtttgag cctgaattgg aagaagaaaa acgaaatgag    1440
ctgtataaag gctggcaaaa agccgtgaaa gcagctatgg cttttaaata a             1491
```

<210> SEQ ID NO 9
<211> LENGTH: 377
<212> TYPE: PRT
<213> ORGANISM: Artificial Sequence
<220> FEATURE:
<223> OTHER INFORMATION: Protein translated from synthetic DNA

<400> SEQUENCE: 9

```
Met Lys Arg Ile Leu Cys Ile Thr Gly Thr Arg Ala Asp Phe Gly Lys
1               5                   10                  15

Leu Lys Pro Leu Leu Ala Tyr Ile Glu Asn His Pro Asp Leu Glu Leu
            20                  25                  30

His Leu Ile Val Thr Gly Met His Met Lys Thr Tyr Gly Arg Thr
        35                  40                  45

Tyr Lys Glu Val Thr Arg Glu Asn Tyr Gln His Thr Tyr Leu Phe Ser
    50                  55                  60

Asn Gln Ile Gln Gly Glu Pro Met Gly Ala Val Leu Gly Asn Thr Ile
65                  70                  75                  80

Thr Phe Ile Ser Arg Leu Ser Asp Glu Ile Glu Pro Asp Met Val Met
                85                  90                  95

Ile His Gly Asp Arg Leu Glu Ala Leu Ala Gly Ala Ala Val Gly Ala
            100                 105                 110

Leu Ser Ser Arg Leu Val Cys His Ile Glu Gly Gly Glu Leu Ser Gly
        115                 120                 125

Thr Val Asp Asp Ser Ile Arg His Ser Ile Ser Lys Leu Ser His Ile
    130                 135                 140

His Leu Val Ala Asn Glu Gln Ala Val Thr Arg Leu Val Gln Met Gly
145                 150                 155                 160

Glu Lys Arg Lys His Ile His Ile Gly Ser Pro Asp Leu Asp Val
                165                 170                 175

Met Ala Ser Ser Thr Leu Pro Ser Leu Glu Glu Val Lys Glu Tyr Tyr
            180                 185                 190

Gly Leu Pro Tyr Glu Asn Tyr Gly Ile Ser Met Phe His Pro Val Thr
        195                 200                 205

Thr Glu Ala His Leu Met Pro Gln Tyr Ala Ala Gln Tyr Phe Lys Ala
    210                 215                 220

Leu Glu Leu Ser Gly Gln Asn Ile Ile Ser Ile Tyr Pro Asn Asn Asp
225                 230                 235                 240

Thr Gly Thr Glu Ser Ile Leu Gln Glu Leu Leu Lys Tyr Gln Ser Asp
                245                 250                 255

Lys Phe Ile Ala Phe Pro Ser Ile Arg Phe Glu Tyr Phe Leu Val Leu
            260                 265                 270
```

```
Leu Lys His Ala Lys Phe Met Val Gly Asn Ser Ser Ala Gly Ile Arg
                275                 280                 285

Glu Ala Pro Leu Tyr Gly Val Pro Ser Ile Asp Val Gly Thr Arg Gln
        290                 295                 300

Ser Asn Arg His Met Gly Lys Ser Ile Ile His Thr Asp Tyr Glu Thr
305                 310                 315                 320

Lys Asn Ile Phe Asp Ala Ile Gln Gln Ala Cys Ser Leu Gly Lys Phe
                325                 330                 335

Glu Ala Asp Asp Thr Phe Asn Gly Gly Asp Thr Arg Thr Ser Thr Glu
            340                 345                 350

Arg Phe Ala Glu Val Ile Asn Asn Pro Glu Thr Trp Asn Val Ser Ala
        355                 360                 365

Gln Lys Arg Phe Ile Asp Leu Asn Leu
    370                 375

<210> SEQ ID NO 10
<211> LENGTH: 1134
<212> TYPE: DNA
<213> ORGANISM: Artificial Sequence
<220> FEATURE:
<223> OTHER INFORMATION: Synthetic DNA

<400> SEQUENCE: 10
atgaaaagaa ttttatgcat cacaggaaca cgcgcagatt ttggcaaact gaaaccgctg      60
cttgcgtata ttgaaaatca tccggatctg gaacttcatt taatcgttac aggaatgcat     120
atgatgaaaa catacggcag aacatacaaa gaagtgacac gcgaaaacta ccaacataca     180
tacctgtttt caaaccaaat tcagggcgaa ccgatgggag cagtgctggg caacacaatc     240
acatttatct ctagactttc agatgaaatc gaaccggata tggtcatgat ccatggagat     300
agacttgaag cattagcggg agcagcggtg ggcgcgttat caagccgcct ggtctgtcat     360
attgaaggcg gagaattaag cggcacagtc gatgattcta ttcgccattc aatcagcaaa     420
cttagccata tccatctggt tgctaacgaa caagccgtta caagacttgt gcagatggga     480
gaaaaacgca acatatcca tattatcggc tcaccggatt tagatgtgat ggcttcttca     540
acactgccga gccttgaaga agtcaaagaa tattatggac tgccgtacga aaactacggc     600
atctcaatgt tcatccggt acaacagaa gctcatctta tgccgcaata tgctgcccag     660
tattttaaag ccctggaact ttcaggacag aacattatca gcatttatcc gaataacgat     720
acaggcacag aaagcatcct tcaagaactg ctgaaatacc agagcgataa atttatcgct     780
tttccgtcta tcagatttga atattttctg gttcttctga acatgccaa atttatggtg     840
ggaaatagct ctgctggcat tcgcgaagcc cgctgtatg gagtcccgag catcgatgtt     900
ggcacaagac aatctaatcg ccatatggga aaatcaatca tccatacaga ttacgaaaca     960
aaaaacattt ttgatgcaat ccaacaggcg tgctctctgg gcaaatttga agcagatgat    1020
acatttaacg gcggagatac aagaacatct acagaacgct ttgcagaagt cattaataac    1080
ccggaaacat ggaatgtttc agcgcagaaa agatttatcg atttaaacct gtaa          1134

<210> SEQ ID NO 11
<211> LENGTH: 229
<212> TYPE: PRT
<213> ORGANISM: Artificial Sequence
<220> FEATURE:
<223> OTHER INFORMATION: Protein translated from synthetic DNA

<400> SEQUENCE: 11
```

```
Met Ser Leu Leu Ala Gln Leu Asp Gln Lys Ile Ala Ala Asn Gly Gly
1               5                   10                  15
Leu Ile Val Ser Cys Gln Pro Val Pro Asp Ser Pro Leu Asp Lys Pro
            20                  25                  30
Glu Ile Val Ala Ala Met Ala Leu Ala Ala Glu Gln Ala Gly Ala Val
        35                  40                  45
Ala Ile Arg Ile Glu Gly Val Ala Asn Leu Gln Ala Thr Arg Ala Val
    50                  55                  60
Val Ser Val Pro Ile Gly Ile Val Lys Arg Asp Leu Glu Asp Ser
65                  70                  75                  80
Pro Val Arg Ile Thr Ala Tyr Ile Glu Asp Val Asp Ala Leu Ala Gln
                85                  90                  95
Ala Gly Ala Asp Ile Ile Ala Ile Asp Gly Thr Asp Arg Pro Arg Pro
            100                 105                 110
Val Pro Val Glu Thr Leu Leu Ala Arg Ile His His His Gly Leu Leu
        115                 120                 125
Ala Met Thr Asp Cys Ser Thr Pro Glu Asp Gly Leu Ala Cys Gln Lys
    130                 135                 140
Leu Gly Ala Glu Ile Ile Gly Thr Thr Leu Ser Gly Tyr Thr Thr Pro
145                 150                 155                 160
Glu Thr Pro Glu Glu Pro Asp Leu Ala Leu Val Lys Thr Leu Ser Asp
                165                 170                 175
Ala Gly Cys Arg Val Ile Ala Glu Gly Arg Tyr Asn Thr Pro Ala Gln
            180                 185                 190
Ala Ala Asp Ala Met Arg His Gly Ala Trp Ala Val Thr Val Gly Ser
    195                 200                 205
Ala Ile Thr Arg Leu Glu His Ile Cys Gln Trp Tyr Asn Thr Ala Met
210                 215                 220
Lys Lys Ala Val Leu
225
```

<210> SEQ ID NO 12
<211> LENGTH: 894
<212> TYPE: DNA
<213> ORGANISM: Artificial Sequence
<220> FEATURE:
<223> OTHER INFORMATION: Synthetic DNA

<400> SEQUENCE: 12

```
atggcaacga atttacgtgg cgtaatggct gcactcctga ctccttttga ccaacaacaa      60
gcactggata aagcgagtct gcgtcgcctg gttcagttca atattcagca gggcatcgac     120
ggtttatacg tgggtggttc gaccggcgag gcctttgtac aaagcctttc gagcgtgaa      180
caggtactga aaatcgtcgc cgaagaggcg aaaggtaaga ttaaactcat cgcccacgtc     240
ggttgcgtca gcaccgccga aagccaacaa cttgcggcat cggctaaacg ttatggcttc     300
gatgccgtct ccgccgtcac gccgttctac tatcctttca gctttgaaga cactgcgat     360
cactatcggg caattattga ttcggcggat ggtttgccga tggtggtgta caacattcca     420
gccctgagtg gggtaaaaact gaccctggat cagatcaaca cacttgttac attgcctggc     480
gtaggtgcgc tgaaacagac ctctggcgat ctctatcaga tggagcagat ccgtcgtgaa     540
catcctgatc ttgtgctcta taacggttac gacgaaatct tcgcctctgg tctgctggcg     600
ggcgctgatg tggtatcgg cagtacctac aacatcatgg ctggcgcta tcaggggatc     660
gttaaggcgc tgaaagaagg cgatatccag accgcgcaga aactgcaaac tgaatgcaat     720
```

```
aaagtcattg atttactgat caaaacgggc gtattccgcg gcctgaaaac tgtcctccat    780
tatatggatg tcgtttctgt gccgctgtgc cgcaaaccgt ttggaccggt agatgaaaaa    840
tatctgccag aactgaaggc gctggcccag cagttgatgc aagagcgcgg gtga          894
```

<210> SEQ ID NO 13
<211> LENGTH: 346
<212> TYPE: PRT
<213> ORGANISM: Escherichia coli

<400> SEQUENCE: 13

```
Met Ser Asn Ile Tyr Ile Val Ala Glu Ile Gly Cys Asn His Asn Gly
1               5                   10                  15

Ser Val Asp Ile Ala Arg Glu Met Ile Leu Lys Ala Lys Glu Ala Gly
            20                  25                  30

Val Asn Ala Val Lys Phe Gln Thr Phe Lys Ala Asp Lys Leu Ile Ser
        35                  40                  45

Ala Ile Ala Pro Lys Ala Glu Tyr Gln Ile Lys Asn Thr Gly Glu Leu
    50                  55                  60

Glu Ser Gln Leu Glu Met Thr Lys Lys Leu Glu Met Lys Tyr Asp Asp
65                  70                  75                  80

Tyr Leu His Leu Met Glu Tyr Ala Val Ser Leu Asn Leu Asp Val Phe
                85                  90                  95

Ser Thr Pro Phe Asp Glu Asp Ser Ile Asp Phe Leu Ala Ser Leu Lys
            100                 105                 110

Gln Lys Ile Trp Lys Ile Pro Ser Gly Glu Leu Leu Asn Leu Pro Tyr
        115                 120                 125

Leu Glu Lys Ile Ala Lys Leu Pro Ile Pro Asp Lys Lys Ile Ile Ile
    130                 135                 140

Ser Thr Gly Met Ala Thr Ile Asp Glu Ile Lys Gln Ser Val Ser Ile
145                 150                 155                 160

Phe Ile Asn Asn Lys Val Pro Val Gly Asn Ile Thr Ile Leu His Cys
                165                 170                 175

Asn Thr Glu Tyr Pro Thr Pro Phe Glu Asp Val Asn Leu Asn Ala Ile
            180                 185                 190

Asn Asp Leu Lys Lys His Phe Pro Lys Asn Asn Ile Gly Phe Ser Asp
        195                 200                 205

His Ser Ser Gly Phe Tyr Ala Ala Ile Ala Ala Val Pro Tyr Gly Ile
    210                 215                 220

Thr Phe Ile Glu Lys His Phe Thr Leu Asp Lys Ser Met Ser Gly Pro
225                 230                 235                 240

Asp His Leu Ala Ser Ile Glu Pro Asp Glu Leu Lys His Leu Cys Ile
                245                 250                 255

Gly Val Arg Cys Val Glu Lys Ser Leu Gly Ser Asn Ser Lys Val Val
            260                 265                 270

Thr Ala Ser Glu Arg Lys Asn Lys Ile Val Ala Arg Lys Ser Ile Ile
        275                 280                 285

Ala Lys Thr Glu Ile Lys Lys Gly Glu Val Phe Ser Glu Lys Asn Ile
    290                 295                 300

Thr Thr Lys Arg Pro Gly Asn Gly Ile Ser Pro Met Glu Trp Tyr Asn
305                 310                 315                 320

Leu Leu Gly Lys Ile Ala Glu Gln Asp Phe Ile Pro Asp Glu Leu Ile
                325                 330                 335

Ile His Ser Glu Phe Lys Asn Gln Gly Glu
            340                 345
```

<210> SEQ ID NO 14
<211> LENGTH: 1041
<212> TYPE: DNA
<213> ORGANISM: Escherichia coli

<400> SEQUENCE: 14

```
atgtctaaca tctacatcgt ggcagaaatc ggctgcaatc ataacggatc agtcgatatc      60
gcgagagaaa tgattttaaa agctaaagaa gccggcgtga acgctgtcaa atttcaaaca     120
tttaaagccg ataaactgat cagcgcaatt gcgccgaaag cagaatacca aatcaaaaac     180
acaggagaat tagaatctca gctggaaatg acgaaaaaac tggaaatgaa atacgatgat     240
taccttcatc tgatggaata cgcagtcagc ctgaatcttg atgtttttag cacaccgttt     300
gatgaagatt ctattgattt tctggcgtca ctgaaacaaa aatctggaa aattccgtca     360
ggcgaactgc ttaaccttcc gtacctggaa aaatcgcta aacttccgat cccggataag     420
aaaattatca ttagcacagg catggccaca atcgatgaaa tcaaacagtc tgtctcaatc     480
tttatcaata caaagtcccc ggttggaaac atcacaatcc tgcattgtaa cacagaatat     540
ccgacaccgt tgaagatgt taaccttaac gctatcaacg atctgaaaaa acattttccg     600
aaaaacaaca tcggcttttc tgatcattca agcggatttt atgcagcgat tgctgccgtt     660
ccgtatggca tcacatttat cgaaaaacat tttacactgg ataaaagcat gtctggaccg     720
gatcatcttg cttcaatcga accggatgaa ctgaaacatc tttgcattgg cgttagatgt     780
gtggaaaaat cactgggatc aaatagcaaa gttgtgacag ccagcgaaag aaaaaacaaa     840
atcgttgcac gcaaatctat catcgcgaaa acagaaatca aaaaggaga gtgttttca     900
gagaaaaata tcacaacaaa aagaccgggc aacggaatta gcccgatgga atggtataat     960
ttactgggca aaatcgcgga acaagatttt atcccggatg aacttatcat ccatagcgaa    1020
tttaaaaacc agggagaata a                                              1041
```

<210> SEQ ID NO 15
<211> LENGTH: 347
<212> TYPE: PRT
<213> ORGANISM: Moritella viscosa

<400> SEQUENCE: 15

```
Met Thr Asn Pro Val Phe Glu Ile Ser Gly Arg Lys Val Gly Leu Asp
1               5                   10                  15

Tyr Ala Pro Leu Val Ile Ala Glu Ile Gly Ile Asn His Glu Gly Ser
            20                  25                  30

Leu Lys Thr Ala Phe Glu Met Val Asp Ala Ala Ile Glu Gly Gly Ala
        35                  40                  45

Glu Ile Ile Lys His Gln Thr His Val Ile Glu Asp Glu Met Ser Ser
    50                  55                  60

Glu Ala Lys Lys Val Ile Pro Gly Asn Ala Asp Val Ser Ile Tyr Glu
65                  70                  75                  80

Ile Met Asp Arg Cys Ser Leu Asn Glu Glu Asp Glu Ile Lys Leu Lys
                85                  90                  95

Lys Tyr Ile Glu Ser Lys Gly Ala Ile Phe Ile Ser Thr Pro Phe Ser
            100                 105                 110

Arg Ala Ala Ala Leu Arg Leu Glu Arg Met Gly Val Ser Ala Tyr Lys
        115                 120                 125

Ile Gly Ser Gly Glu Cys Asn Asn Tyr Pro Leu Leu Asp Leu Ile Ala
    130                 135                 140
```

Ser Tyr Gly Lys Pro Val Ile Leu Ser Thr Gly Met Asn Asp Ile Pro
145                 150                 155                 160

Ser Ile Arg Lys Ser Val Glu Ile Phe Arg Lys Tyr Lys Thr Pro Leu
            165                 170                 175

Cys Leu Leu His Thr Thr Asn Leu Tyr Pro Thr Pro Asp His Leu Ile
        180                 185                 190

Arg Ile Gly Ala Met Glu Glu Met Gln Arg Glu Phe Ser Asp Val Val
            195                 200                 205

Val Gly Leu Ser Asp His Ser Ile Asp Asn Leu Ala Cys Leu Gly Ala
        210                 215                 220

Val Ala Ala Gly Ala Ser Val Leu Glu Arg His Phe Thr Asp Asn Lys
225                 230                 235                 240

Ala Arg Ser Gly Pro Asp Ile Cys Cys Ser Met Asp Gly Ala Glu Cys
            245                 250                 255

Ala Glu Leu Ile Ser Gln Ser Lys Arg Met Ala Gln Met Arg Gly Gly
        260                 265                 270

Ser Lys Gly Ala Val Lys Glu Glu Gln Val Thr Ile Asp Phe Ala Tyr
    275                 280                 285

Ala Ser Val Val Thr Ile Lys Glu Ile Lys Ala Gly Glu Ala Phe Thr
        290                 295                 300

Lys Asp Asn Leu Trp Val Lys Arg Pro Gly Thr Gly Asp Phe Leu Ala
305                 310                 315                 320

Asp Asp Tyr Glu Met Leu Leu Gly Lys Lys Ala Ser Gln Asn Ile Asp
            325                 330                 335

Phe Asp Val Gln Leu Lys Lys Glu Phe Ile Lys
        340                 345

<210> SEQ ID NO 16
<211> LENGTH: 1044
<212> TYPE: DNA
<213> ORGANISM: Moritella viscosa

<400> SEQUENCE: 16
atgacaaatc cggtctttga aatttctggc agaaaagttg gacttgatta tgccccgtta 60
gtgatcgcag aaattggcat caaccatgaa ggatcactga aaacagcctt tgaaatggtg 120
gatgcagcga ttgaaggcgg agcagaaatc atcaaacatc aaacacatgt cattgaagat 180
gaaatgtcaa gcgaagcaaa gaaagttatc ccgggcaatg ctgatgtgag catctacgaa 240
atcatggata gatgctctct gaacgaagaa gatgaaatca aactgaaaaa atacatcgaa 300
tcaaaaggcg ctatctttat ctcaacaccg tttagccgcg ctgccgcact gagacttgaa 360
cgcatgggag ttagcgccta taaaattggc tctggagaat gcaataacta tccgctgctt 420
gatcttattg cgtcttatgg caaaccggtc atcttatcaa caggaatgaa tgatattccg 480
tctatcagaa aatcagttga aatctttcgc aaatacaaaa caccgctttg tttactgcat 540
acaacaaacc tgtatccgac accggatcat cttattagaa tcggcgcaat ggaagaaatg 600
caacgcgaat ttagcgatgt tgtggtcgga ctgagcgatc attctatcga taacctggct 660
tgtctgggag ctgtggctgc tggagcttct gtcctggaaa gacattttac agataacaaa 720
gctcgctcag gcccggatat ttgctgtagc atggatggag cggaatgtgc tgaacttatc 780
tctcaatcaa aaagaatggc ccagatgcgc ggcggatcaa aaggcgcagt caaagaagaa 840
caggttacaa ttgattttgc ctatgcaagc gttgtgacaa ttaaagaaat caaagccgga 900
gaagcattta caaaagataa tctgtgggtt aaacgcccgg gcacaggaga ttttcttgcg 960

```
gatgattatg aaatgctttt aggcaagaaa gcaagccaaa acattgattt tgatgtgcag    1020
ctgaagaaag aatttatcaa ataa                                          1044

<210> SEQ ID NO 17
<211> LENGTH: 116
<212> TYPE: DNA
<213> ORGANISM: Artificial Sequence
<220> FEATURE:
<223> OTHER INFORMATION: Synthetic DNA

<400> SEQUENCE: 17
tcatagacct gaaaaggtct ttttttgtac tcttaataat aaaaagaaga tgaaacttgt    60
ttaaggattg aacgtagtag ataataatat taaaactgag aaaggaggtg ataaaa       116

<210> SEQ ID NO 18
<211> LENGTH: 116
<212> TYPE: DNA
<213> ORGANISM: Artificial Sequence
<220> FEATURE:
<223> OTHER INFORMATION: Synthetic DNA

<400> SEQUENCE: 18
attattctta actttacga aactttgata taataacaaa cgtatatatt agtaatttac    60
ggcttatttt ccttgtgagc gtaaaaataa atgtgactat aaaggaggtg ataaaa       116

<210> SEQ ID NO 19
<211> LENGTH: 121
<212> TYPE: DNA
<213> ORGANISM: Artificial Sequence
<220> FEATURE:
<223> OTHER INFORMATION: Synthetic DNA

<400> SEQUENCE: 19
aaacaatgaa actttttttt ataaaaaacg actattttag gatttcattc ttgtattaaa    60
tagagttgta tttattggaa atttaactca taatgaaagt aatttaaagg aggtgataaa   120
a                                                                  121

<210> SEQ ID NO 20
<211> LENGTH: 109
<212> TYPE: DNA
<213> ORGANISM: Artificial Sequence
<220> FEATURE:
<223> OTHER INFORMATION: Synthetic DNA

<400> SEQUENCE: 20
ttttcttgac gccctttga gggaggagta aaatgaaatt gtcaataaat cttaataaag     60
tgcttacaat tgaaagaagt gggggaagag attaaaggag gtgataaaa              109

<210> SEQ ID NO 21
<211> LENGTH: 300
<212> TYPE: DNA
<213> ORGANISM: Artificial Sequence
<220> FEATURE:
<223> OTHER INFORMATION: Synthetic DNA

<400> SEQUENCE: 21
tgataggtgg tatgtttttcg cttgaacttt taaatacagc cattgaacat acggttgatt   60
taataactga caaacatcac cctcttgcta aagcggccaa ggacgccgcc gccggggctg   120
tttgcgttct tgccgtgatt tcgtgtacca ttggtttact tattttttg ccaaggctgt    180
```

```
aatggctgaa aattcttaca tttattttac attttagaa atgggcgtga aaaaaagcgc        240
gcgattatgt aaaatataaa gtgatagcgg taccattata ggtaagagag gaatgtacac        300
```

<210> SEQ ID NO 22
<211> LENGTH: 116
<212> TYPE: DNA
<213> ORGANISM: Artificial Sequence
<220> FEATURE:
<223> OTHER INFORMATION: Synthetic DNA

<400> SEQUENCE: 22

```
ttttcgaatg attaaatttt tgttttttta taaaggtttt ttactatttt gtgaacaatc         60
aaggtagaat caaattgcaa acagtggtaa aatatcgttg aaaggaggtg ataaaa           116
```

<210> SEQ ID NO 23
<211> LENGTH: 97
<212> TYPE: DNA
<213> ORGANISM: Artificial Sequence
<220> FEATURE:
<223> OTHER INFORMATION: Synthetic DNA

<400> SEQUENCE: 23

```
ttgaggaatc atagaatttt gacttaaaaa tttcagttgc ttaatcctac aattcttgat         60
ataatattct catagtttga aaaggaggt gataaaa                                  97
```

<210> SEQ ID NO 24
<211> LENGTH: 113
<212> TYPE: DNA
<213> ORGANISM: Artificial Sequence
<220> FEATURE:
<223> OTHER INFORMATION: Synthetic DNA

<400> SEQUENCE: 24

```
aaacaaaatt cgacaaagtt cactgaattt tcacaaaaga tttatgtttc agcaggaatt         60
gtaaagggta aaagagaaat agatacatat ccttaataaa ggaggtgata aaa              113
```

<210> SEQ ID NO 25
<211> LENGTH: 116
<212> TYPE: DNA
<213> ORGANISM: Artificial Sequence
<220> FEATURE:
<223> OTHER INFORMATION: Synthetic DNA

<400> SEQUENCE: 25

```
attttgtcaa aataatttta ttgacaacgt cttattaacg ttgatataat ttaaatttta         60
tttgacaaaa atgggctcgt gttgtacaat aaatgtagtg aaaggaggtg ataaaa           116
```

<210> SEQ ID NO 26
<211> LENGTH: 76
<212> TYPE: DNA
<213> ORGANISM: Artificial Sequence
<220> FEATURE:
<223> OTHER INFORMATION: Synthetic DNA

<400> SEQUENCE: 26

```
aaaaaacggc ctctcgaaat agagggttga cactcttttg agaatatgtt atattatcag         60
aaaggaggtg ataaaa                                                        76
```

<210> SEQ ID NO 27
<211> LENGTH: 40
<212> TYPE: DNA
<213> ORGANISM: Artificial Sequence
<220> FEATURE:
<223> OTHER INFORMATION: Synthetic DNA

<400> SEQUENCE: 27
cggtgtctgt atatcacaaa aatagtgagc agggtaacga                    40

<210> SEQ ID NO 28
<211> LENGTH: 74
<212> TYPE: DNA
<213> ORGANISM: Artificial Sequence
<220> FEATURE:
<223> OTHER INFORMATION: Synthetic DNA

<400> SEQUENCE: 28
cgcaataacg caggcgttct gtgacattaa cttatttcca cctatttgt tacagcgtgt    60 gccactttta tgca                                                    74

<210> SEQ ID NO 29
<211> LENGTH: 90
<212> TYPE: DNA
<213> ORGANISM: Artificial Sequence
<220> FEATURE:
<223> OTHER INFORMATION: Synthetic DNA

<400> SEQUENCE: 29
taacttgtca gactgccggg aaatcccggc agtctttttt ccattaaaac acggcgcttg    60
aacagctttt tttgaatacc ttgtccagct                                   90

<210> SEQ ID NO 30
<211> LENGTH: 27
<212> TYPE: DNA
<213> ORGANISM: Artificial Sequence
<220> FEATURE:
<223> OTHER INFORMATION: Synthetic DNA

<400> SEQUENCE: 30
gcgtcatcgc agtttttgca cctgact                                      27

<210> SEQ ID NO 31
<211> LENGTH: 32
<212> TYPE: DNA
<213> ORGANISM: Artificial Sequence
<220> FEATURE:
<223> OTHER INFORMATION: Synthetic DNA

<400> SEQUENCE: 31
cgtgatatcg tcattcagtc tcttgaacgc ca                                32

<210> SEQ ID NO 32
<211> LENGTH: 79
<212> TYPE: DNA
<213> ORGANISM: Artificial Sequence
<220> FEATURE:
<223> OTHER INFORMATION: Synthetic DNA

<400> SEQUENCE: 32
cgcaataacg caggcgttct gtgacattaa cttatttcat gttcttttta gttagacgat    60
tttaatacaa gcctcgcca                                               79

<210> SEQ ID NO 33
<211> LENGTH: 90
<212> TYPE: DNA
<213> ORGANISM: Artificial Sequence
<220> FEATURE:

<223> OTHER INFORMATION: Synthetic DNA

<400> SEQUENCE: 33
ataacttgtc agactgccgg gaaatcccgg cagtcttttt tccattaaaa cacggcccag     60
tcataaaata gttttcctaa taagacctgg     90

<210> SEQ ID NO 34
<211> LENGTH: 26
<212> TYPE: DNA
<213> ORGANISM: Artificial Sequence
<220> FEATURE:
<223> OTHER INFORMATION: Synthetic DNA

<400> SEQUENCE: 34
cctacttaag ctgctaccac ttgtga     26

<210> SEQ ID NO 35
<211> LENGTH: 32
<212> TYPE: DNA
<213> ORGANISM: Artificial Sequence
<220> FEATURE:
<223> OTHER INFORMATION: Synthetic DNA

<400> SEQUENCE: 35
cgtgatatcg tcattcagtc tcttgaacgc ca     32

<210> SEQ ID NO 36
<211> LENGTH: 79
<212> TYPE: DNA
<213> ORGANISM: Artificial Sequence
<220> FEATURE:
<223> OTHER INFORMATION: Synthetic DNA

<400> SEQUENCE: 36
cgcaataacg caggcgttct gtgacattaa cttatttcat gttcttttta gttagacgat     60
tttaatacaa gcctcgcca     79

<210> SEQ ID NO 37
<211> LENGTH: 90
<212> TYPE: DNA
<213> ORGANISM: Artificial Sequence
<220> FEATURE:
<223> OTHER INFORMATION: Synthetic DNA

<400> SEQUENCE: 37
ataacttgtc agactgccgg gaaatcccgg cagtcttttt tccattaaaa cacggcccag     60
tcataaaata gttttcctaa taagacctgg     90

<210> SEQ ID NO 38
<211> LENGTH: 26
<212> TYPE: DNA
<213> ORGANISM: Artificial Sequence
<220> FEATURE:
<223> OTHER INFORMATION: Synthetic DNA

<400> SEQUENCE: 38
ataaccaacg cagcaagtgg caacct     26

<210> SEQ ID NO 39
<211> LENGTH: 38
<212> TYPE: DNA
<213> ORGANISM: Artificial Sequence
<220> FEATURE:
<223> OTHER INFORMATION: Synthetic DNA

<400> SEQUENCE: 39
gtcgtactgc catctgtttc tgtatacatt ctcccaat          38

<210> SEQ ID NO 40
<211> LENGTH: 72
<212> TYPE: DNA
<213> ORGANISM: Artificial Sequence
<220> FEATURE:
<223> OTHER INFORMATION: Synthetic DNA

<400> SEQUENCE: 40
cgcaataacg caggcgttct gtgacattaa cttatttctt tttaccttgt gataaacagg          60
cacatgacgg ca          72

<210> SEQ ID NO 41
<211> LENGTH: 90
<212> TYPE: DNA
<213> ORGANISM: Artificial Sequence
<220> FEATURE:
<223> OTHER INFORMATION: Synthetic DNA

<400> SEQUENCE: 41
gaataacttg tcagactgcc gggaaatccc ggcagtcttt tttccattaa aacacggccc          60
gctgtccttg ttttttcag tcaatattgc          90

<210> SEQ ID NO 42
<211> LENGTH: 27
<212> TYPE: DNA
<213> ORGANISM: Artificial Sequence
<220> FEATURE:
<223> OTHER INFORMATION: Synthetic DNA

<400> SEQUENCE: 42
gacatttgca gcgccggtta tcgctca          27

<210> SEQ ID NO 43
<211> LENGTH: 29
<212> TYPE: DNA
<213> ORGANISM: Artificial Sequence
<220> FEATURE:
<223> OTHER INFORMATION: Synthetic DNA

<400> SEQUENCE: 43
gcgaacaggc atcctataca ctgggacaa          29

<210> SEQ ID NO 44
<211> LENGTH: 59
<212> TYPE: DNA
<213> ORGANISM: Artificial Sequence
<220> FEATURE:
<223> OTHER INFORMATION: Synthetic DNA

<400> SEQUENCE: 44
accgagctcg aattcttatt agacggagtc ttttttgctt ttgccaatca gacgtgtaa          59

<210> SEQ ID NO 45
<211> LENGTH: 90
<212> TYPE: DNA
<213> ORGANISM: Artificial Sequence
<220> FEATURE:
<223> OTHER INFORMATION: Synthetic DNA

<400> SEQUENCE: 45

```
acttgtcaga ctgccgggaa atcccggcag tctttttcc attaaaacac ggcgacggag    60 tctttttta tttcgttttt aagaagtagg                                      90
```

<210> SEQ ID NO 46
<211> LENGTH: 34
<212> TYPE: DNA
<213> ORGANISM: Artificial Sequence
<220> FEATURE:
<223> OTHER INFORMATION: Synthetic DNA

<400> SEQUENCE: 46

```
ctaacacaat ccattttgaa gatgcctttt tgca                                34
```

<210> SEQ ID NO 47
<211> LENGTH: 34
<212> TYPE: DNA
<213> ORGANISM: Artificial Sequence
<220> FEATURE:
<223> OTHER INFORMATION: Synthetic DNA

<400> SEQUENCE: 47

```
gtgttcgtag tctctcggga gagtcattcc atga                                34
```

<210> SEQ ID NO 48
<211> LENGTH: 70
<212> TYPE: DNA
<213> ORGANISM: Artificial Sequence
<220> FEATURE:
<223> OTHER INFORMATION: Synthetic DNA

<400> SEQUENCE: 48

```
cgcaataacg caggcgttct gtgacattaa cttatttcgc gtttaagaga acaggccttg    60
gtttgtgaca                                                           70
```

<210> SEQ ID NO 49
<211> LENGTH: 83
<212> TYPE: DNA
<213> ORGANISM: Artificial Sequence
<220> FEATURE:
<223> OTHER INFORMATION: Synthetic DNA

<400> SEQUENCE: 49

```
gaataacttg tcagactgcc gggaaatccc ggcagtcttt tttccattaa aacacggcat    60
gactgtcagt tctttcagcc gct                                            83
```

<210> SEQ ID NO 50
<211> LENGTH: 36
<212> TYPE: DNA
<213> ORGANISM: Artificial Sequence
<220> FEATURE:
<223> OTHER INFORMATION: Synthetic DNA

<400> SEQUENCE: 50

```
caacgattgc gtttaatgtc agcatcagcc cataca                              36
```